(12) United States Patent
Jabbour et al.

(10) Patent No.: US 8,267,917 B2
(45) Date of Patent: Sep. 18, 2012

(54) PERCUTANEOUSLY RETRIEVABLE STENT ASSEMBLY WITH FLUID DRAINING CAPABILITY

(75) Inventors: Nicolas Jabbour, Pasadena, CA (US); Samuel M. Shaolian, Newport Beach, CA (US)

(73) Assignee: University of Southern California, Los Angeles, CA (US)

( * ) Notice: Subject to any disclaimer, the term of this patent is extended or adjusted under 35 U.S.C. 154(b) by 516 days.

(21) Appl. No.: 11/191,745

(22) Filed: Jul. 27, 2005

(65) Prior Publication Data
US 2006/0129223 A1 Jun. 15, 2006

Related U.S. Application Data

(60) Provisional application No. 60/591,787, filed on Jul. 27, 2004.

(51) Int. Cl.
*A61M 27/00* (2006.01)
(52) U.S. Cl. .......................................... 604/540
(58) Field of Classification Search .................. 604/341, 604/350, 355, 540
See application file for complete search history.

(56) References Cited

U.S. PATENT DOCUMENTS

| | | | | |
|---|---|---|---|---|
| 5,129,910 A * | 7/1992 | Phan et al. | | 606/127 |
| 5,151,105 A * | 9/1992 | Kwan-Gett | | 623/1.32 |
| 5,259,847 A | 11/1993 | Trambert | | 604/164 |
| 5,302,168 A * | 4/1994 | Hess | | 600/3 |
| 5,354,263 A | 10/1994 | Coll | | 604/8 |
| 5,401,257 A | 3/1995 | Chevalier et al. | | 604/265 |
| 5,486,191 A | 1/1996 | Pasricha et al. | | 606/191 |
| 5,534,007 A * | 7/1996 | St. Germain et al. | | 623/1.11 |
| 5,618,266 A * | 4/1997 | Liprie | | 604/21 |
| 5,693,065 A | 12/1997 | Rains, III | | 606/196 |
| 5,897,911 A * | 4/1999 | Loeffler | | 427/2.25 |
| 5,902,299 A * | 5/1999 | Jayaraman | | 606/20 |
| 5,954,745 A * | 9/1999 | Gertler et al. | | 606/200 |
| 6,090,072 A * | 7/2000 | Kratoska et al. | | 604/164.01 |
| 6,132,471 A | 10/2000 | Johlin, Jr. | | 623/23.64 |
| 6,254,628 B1 * | 7/2001 | Wallace et al. | | 623/1.12 |
| 6,579,305 B1 | 6/2003 | Lashinski | | |
| 6,770,066 B1 | 8/2004 | Weaver et al. | | 605/509 |
| 2001/0049517 A1 * | 12/2001 | Zadno-Azizi et al. | | 604/509 |
| 2002/0161341 A1 | 10/2002 | Stinson et al. | | 604/264 |
| 2003/0069533 A1 | 4/2003 | Kakutani et al. | | 604/540 |
| 2003/0120331 A1 * | 6/2003 | Chobotov et al. | | 623/1.13 |

OTHER PUBLICATIONS

International Search Report for corresponding WO application PCT/US05/26769 lists the reference above.

* cited by examiner

*Primary Examiner* — Tatyana Zalukaeva
*Assistant Examiner* — Benedict L Hanrahan
(74) *Attorney, Agent, or Firm* — DLA Piper LLP (US)

(57) ABSTRACT

The present invention provides a stent assembly for expanding a bodily passage in a patient and draining a fluid therefrom. The assembly comprises at least one expandable stent and an elongated carrier for delivery or retrieval of the stent. The stent is circumferentially attached to a distal end of the carrier. The carrier defines at least two concentric lumens therethrough, a drainage lumen in fluid communication with the bodily passage for drainage of the fluid and an inflation lumen in fluid communication with the expandable stent. The invention also provides a method of expanding a bodily passage in a patient and draining a fluid therefrom. The method comprises providing a stent assembly of the present invention; inserting a guidewire into the bodily passage through the drainage lumen of the carrier; advancing the assembly along the guidewire until the assembly reaches a desired location; expanding the stent; and draining the fluid through drainage lumen of the carrier.

27 Claims, 8 Drawing Sheets

PERCUTANEOUSLY RETRIEVABLE STENT ASSEMBLY WITH FLUID DRAINING CAPABILITY

This application claims priority to the U.S. Provisional Patent Application No. 60/591,787, filed on Jul. 27, 2004.

FIELD OF THE INVENTION

This invention relates to devices and methods for expanding a bodily passage in a patient and draining a fluid therefrom. In particular, the invention is directed to percutaneously retrievable stent assemblies with expandable stents.

BACKGROUND OF THE INVENTION

A number of disorders are characterized by formation of stenosis, strictures, or aneurysms that prevent normal passage and draining of fluids in body blood vessels and other tubular body structures, such as the esophagus, bile and kidney ducts, urinary tract, gastrointestinal (GI) tract, sinus pathway, and the tracheo-bronchial tree. When a tubular body structure becomes occluded, it is often desirable to dilate the occluded area and facilitate drainage of fluids therethrough. Although surgical methods are available for removing an occlusion or for a complete removal of a narrowed area and restoring normal fluid flow, it involves general anesthesia that may not be suitable for all patients and may also result in formation of secondary strictures from local surgical scars. Some of such secondary strictures may not be amendable to further surgery due to their difficult location or due to the underlying patient condition.

An alternative treatment that avoids many complications of a surgery, involves a two-step procedure in which stricture is first dilated and then a stent is inserted. Typically, stents are longitudinal cylindrical devices formed of biocompatible material, such as metal or plastic. Although conventional stents usually allow a patient to avoid a surgical treatment, they have several limitations. For example, when metal stents are used to treat occlusions in biliary or procreatic ducts, they cannot be removed or replaced. When left in place, they often lead to development of sludge and epithelial proliferation that result in severe stricture and restenosis of the biliary system at the stent site. Accordingly, conventional metal stents are usually used in patients with malignant tumors who are not expected to survive for a prolonged period of time.

The presently available plastic stents for treatment of occlusions in biliary or procreatic ducts also have significant limitations. They are stiff and once inserted percutaneously, the drain usually runs in the intercoastal space and leads to a significant discomfort to the patient. Furthermore, similarly to the metal stents, plastic stents often cause a premature occlusion from sludge and stone formation, which may result in a biliary infection. Although these stents provide significant dilatation of the biliary system, they lead to significant recurrence of the stricture in over 50% of the patients.

SUMMARY OF THE INVENTION

As it becomes apparent from the discussion above, both metal and plastic conventional stents suffer from a number of shortcomings. Additionally, although conventional stents may be used for draining fluids, such as bile, they cannot be used for a stricture dilation. Usually, a separate balloon catheter is used to dilate a stricture prior to an insertion of a stent. Once inserted, the catheter does not provide any further increase in size of the narrowing without further intervention. Furthermore, because the diameter of the catheter used to maintain the dilatation of the narrowed area is the same throughout the length of the catheter, a larger passage in the body is required, which may lead to complications, including infections and formation of secondary strictures.

Accordingly, it is an object of the present invention to provide an improved stent assembly, which can be placed atraumatically within an occluded bodily passage to provide both dilation of the passage and draining of a fluid therefrom, and which further can be removed without damaging the passage. It is also an object of the present invention to provide a convenient method of expanding a bodily passage in a patient and draining a fluid therefrom.

These and other objects and advantages are achieved in a stent assembly of the present invention. The assembly comprises at least one expandable stent and an elongated carrier for delivery or retrieval of the stent. The stent is circumferentially attached to a distal end of the carrier. The carrier defines at least two concentric lumens therethrough, a drainage lumen in fluid communication with the bodily passage for drainage of the fluid and an inflation lumen in fluid communication with the expandable stent. In one embodiment, the drainage lumen is sized to accommodate a removable guidewire. In another embodiment, the carrier further comprises a separate guidewire lumen sized to accommodate a guidewire.

The inflation lumen may further include inflation holes located within an orthogonal projection of the stent onto the inflation lumen of the carrier. The drainage lumen may communicate with the bodily passage through a plurality of drainage holes connecting an outer surface of the carrier with the drainage lumen.

In one embodiment, the stent forms a spiral about the carrier. In another embodiment, a plurality of expandable stents is circumferentially attached to the distal end of the carrier. The stent may be permanently affixed to or be detachable from the carrier.

In another aspect, the present invention provides a method of expanding a bodily passage in a patient and draining a fluid therefrom. The method comprises: (a) providing a stent assembly of the present invention; (b) inserting a guidewire into the bodily passage through the drainage lumen of the carrier; (c) advancing the assembly along the guidewire until the assembly reaches a desired location; (d) expanding the stent; and (e) draining the fluid through drainage lumen of the carrier. In one embodiment, the method further comprises a step of retrieving the stent percutaneously. The retrieved stent may be replaced with a new stent, such that the new stent, when expanded, has a size that is larger than the size of the retrieved stent.

In one embodiment, the stent is permanently affixed to the carrier and the method further comprises steps of deflating the stent, removing the assembly over the guidewire, inserting a new assembly over the guidewire, and expanding a new stent of the new assembly. In another embodiment, the stent is detachable from the carrier and the method further comprises a step of disengaging the carrier from the stent after the stent is inflated and removing the carrier over the guidewire. In case of a treatment of a biliary stricture, the stent assembly of the present invention may be inserted into a biliary duct using conventional techniques such as Percutaneous Transhepatic Cholangiography (PTC) or Endoscopic Retrograde Cholangio-pancreatography (ERCP).

The stent assembly of the present invention and methods of its use provide a number of advantages over conventional stents and methods, including a lower risk of stricture recurrence. By combining both the dilatation and draining capabilities, the stent assemblies of the present invention are safer and easier to use. For example, when used to treat stricture of a biliary duct, the stent assembly of the present invention allows to maintain the stricture with gradual continuous or intermittent expansion of the stent without the need for repetitive stent removal and reinsertion procedures. When such removal and reinsertion is required, the stent assembly of the present invention allows to replace a stent with a minimal discomfort to the patient by deflating the original stent to remove it and by inflating a new stent only after it is in a desired location inside the passage. Furthermore, because an expandable stent itself is used to dilate the stricture instead of a separate balloon catheter, a soft catheter with a smaller than conventional diameter may be used to provide drainage of bile fluid.

In sum, stent assemblies of the present invention result in better dilatation, less sludge formation, lower risk of infection, and minimal pain since the exteriorized portion is soft and small in size regardless of the size of the stent. These superior results are obtained by combining the two functions of dilatation and drainage, and by allowing progressive and continuous dilatation without the need of repetitive radiological or endoscopic interventions. Once the treatment objective is achieved, usually within a few months, the scent can be removed through the same approach (ERCP or PTC) using the guide wire.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail.

DETAILED DESCRIPTION OF THE PREFERRED EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended. Any alterations and further modifications in the described device, and any further applications of the principles of the invention as described herein are contemplated as would normally occur to one skilled in the art to which the invention relates. The drawings show relative sizes only; measurements and positions are exaggerated for purposes of illustration.

Referring to FIGS. 1a-1d, the present invention provides a stent assembly 10 for expanding a bodily passage 1 in a patient and draining a fluid therefrom. The assembly 10 comprises at least one expandable stent 12 having a first end 13 and a second end 14. The assembly also includes an elongated carrier 11 for delivery or retrieval of the stent 12. The carrier has a distal end 2 and a proximal end 3. The stent 12 is circumferentially attached to the distal end 2 of the carrier 11. The carrier defines at least two concentric lumens therethrough, a drainage lumen 17 in fluid communication with the bodily passage 1 and an inflation lumen 19 in fluid communication with the expandable stent 12. In one embodiment, the drainage lumen 17 is sized to accommodate a removable guidewire, such as a 0.035" Teflon-coated guidewire or any other suitable guideware. In another embodiment, the carrier 11 further comprises a separate guidewire lumen 18 sized to accommodate a guidewire.

The expandable stent 12 may be made from a polymeric material such as polyethylene (PE), nylon or any other resilient material that could be formed into an expandable balloon-shaped vessel with a non-compliant form. In one embodiment, an outer diameter of the stent 12, when expanded, is larger than an internal diameter of the bodily passage 1 to be treated.

The stent assembly 10 of the present invention may be used to treat stenosis, strictures, or aneurysms that prevent normal passage and draining of fluids in body blood vessels and any other tubular body structures including, but not limited to esophagus, bile and kidney ducts, urinary tract, gastrointestinal (GI) tract, sinus pathway, and the tracheo-bronchial tree. The stent assembly 10 of the present invention may also be used in intercraineal applications, such as treatment of brain trauma.

Generally, the size of the carrier and the stent is selected to match the size of the bodily passage being treated. Preferably, an outer diameter of the stent 12, when expanded, is larger than an internal diameter of the bodily passage 1 to be treated. In one embodiment, an outer diameter of the stent 12, when expanded, is larger than an internal diameter of the bodily passage by about 1-2 mm. For example, in one embodiment, the stent assembly 10 is used for treatment of a biliary stricture and to drain biliary tract. In this embodiment, the stent is designed to be larger by 1-2 mm than the diameter of the biliary duct to be treated. An outer diameter of the stent 12 may be from 4 to 12 mm and its length is from 20 to 100 mm, when expanded, and the carrier 11 is a catheter with an outer diameter from 8 to 18 French (2.7 to 6 mm). In another embodiment, in which the stent assembly is used intracranially, an outer diameter of the stent 12 is from 3 to 5 French, when expanded, and the carrier is a catheter with an outer diameter from 2 to 3 French. Those skilled in the art will be able to select appropriate sizes of the stent and the carrier suitable for other applications taking into consideration patient's diagnosis and size of bodily passage to be treated.

The stent 12 could be expanded by any suitable means, including, but not limited to use of various solutions, air, and shape memory materials. In one embodiment, the expandable stent is inflated with a solution of contrast media (Renografin or equivalent 50-50% dilution) at the prescribed pressure (in the range of 10-20 ata).

The carrier may be made from any suitable biocompatible material, including, but not limited to PE, Polyethylene Terephthalate (PET), or polyether block amides, such as Pebax® (Arkema, France) with hardness in the range of 80 A to 50 D (Shore hardness).

The first end 13 and a second end 14 of the stent 12 may have radiopaque marker bands 5, 6 including, but not limited to, those made from heavy metals such as gold, platinum or tantalum. The markers 5 and 6 help to visualize the exact position of the stent 12 under fluoroscopic guidance.

In one embodiment, the inflation lumen 19 communicates with an internal cavity of the stent 12 through inflation skive (s) 7 and/or inflation holes 8 located within an orthogonal projection α of the stent 12 onto the inflation lumen of the carrier. The drainage lumen 17 may communicate with the bodily passage 1 through a plurality of drainage holes 9 connecting an outer surface of the carrier 11 with the drainage lumen 17.

The proximal end 3 of the carrier may be attached to a connector 4 that allows bifurcation of the main shaft lumens into separate side arms. In one embodiment, the connector has a first side arm 103 in a communication with the drainage lumen 17 and a second side arm 101 in a communication with the inflation lumen 19. The free end 106 of the first side arm 103 may be further connected to a fluid collection container, such as a collection bag (not shown).

The free end 107 of the second side arm 101 may be further removably connected to an inflation device (not shown) for inflation or diflation of the stent via a valve connector or a three-way stopcock 109. Such inflation devices are well-known to those skilled in the art. For example, a digital or analog inflation device used routinely in the field of angioplasty may be used. Once the desired inflation pressure within the expandable stent has been achieved, the valve connector may be locked and the inflation device may be disconnected. Preferably, the valve connector allows injection of a solution into the expandable stent while preventing retrograde flow of the solution from the stent when stent is attached to or diasattached from the carrier 11.

In an embodiment, where the carrier further comprises a separate guidewire lumen, the connector 4 further comprises a third side arm 102 in a communication with the guidewire lumen 18 of the carrier. The side arm 102 may be connected to the guidewire lumen via a tapered connector 111.

Figure 1A:
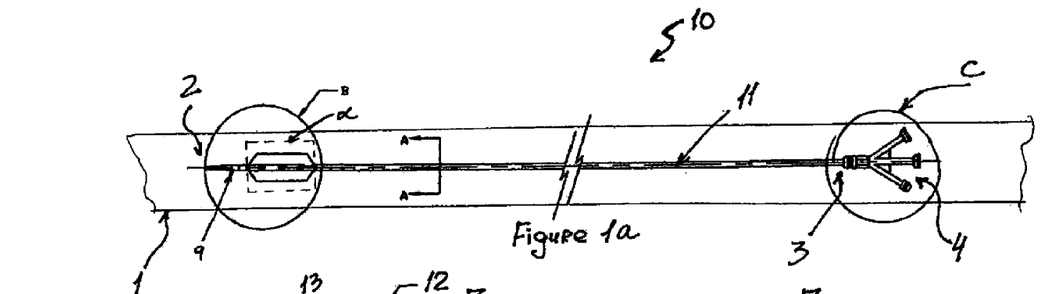
FIGS. 1a-1d depict a stent assembly for expanding a bodily passage in a patient and draining a fluid therefrom, in which the stent is permanently attached to the carrier, in accordance with one embodiment of the present invention.
Figures 1B, 1C, 1D:
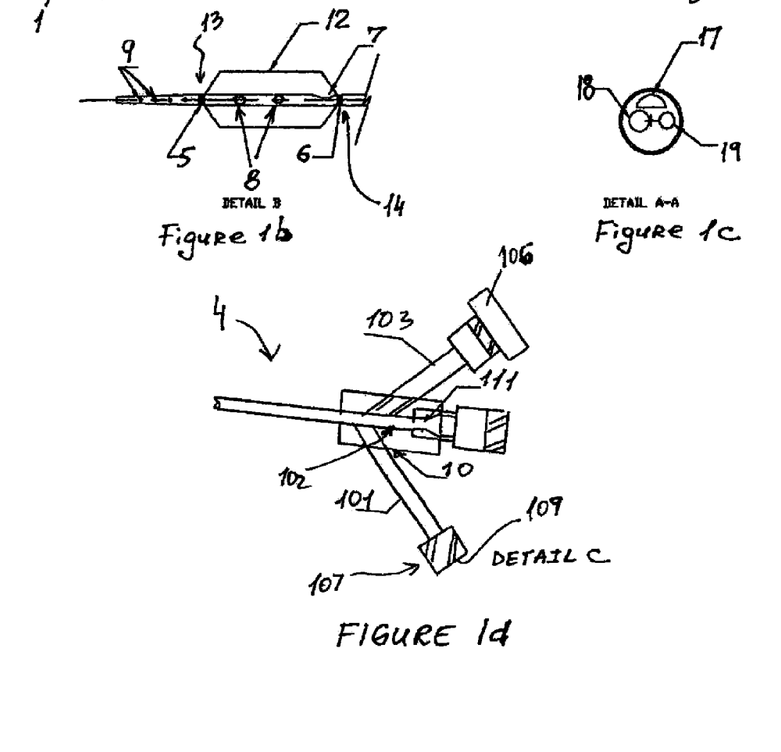
Figure 2A:
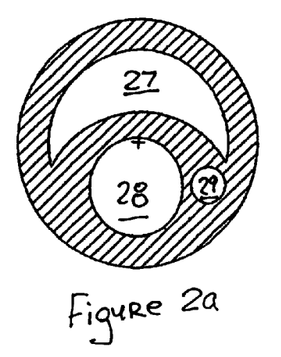
FIGS. 2a-2d show cross sections of the carrier with several possible configurations of lumens according to various embodiments of the present invention.
Figure 2B:
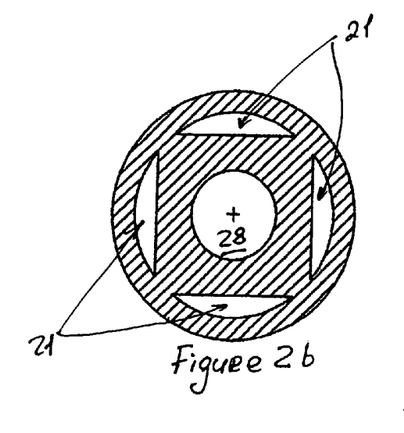
Figure 2C:
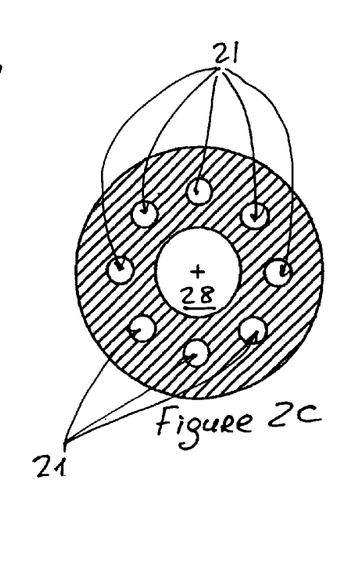
Figure 2D:
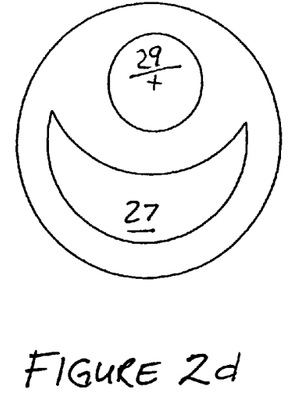

The number, shape, and size of lumens of the present invention are not particularly limited as long as they are capable of performing the assigned function (draining fluid, inflating stent, or providing a passage for a guidewire). In FIGS. 2a-2d, which depict cross section of the carrier, several possible configurations of lumens are exemplified. In an embodiment shown in FIG. 2a, there is a drainage lumen 27, inflation lumen 29, and a guidewire lumen 28. FIGS. 2b and 2c show multi-lumen carriers. The central lumen 28 may be used as a guidewire lumen. Some of lumens 21 may be used as drainage lumens and some as inflation lumens. In certain applications, some of the lumens 21 may be used for any other desirable function. In an embodiment shown in FIG. 2d, the drainage lumen 27 is also used as a guidewire lumen.

The expandable stent of the present invention can be implemented in a variety of configurations as long as, when expanded, they sufficiently engage the bodily passage from within to remain in the desired location while dilating the passage and draining a fluid therefrom. Referring to FIGS. 3a, 3b, 4a, 4b, and 4c, in one embodiment, the stent 42 forms a spiral about the carrier 41. The stent 42 may be fused or glued to an outer surface of the carrier at multiple points 33 of their junction. In this embodiment, the stent 42, when expanded, forms a spiral with an outer diameter preferably exceeding the diameter of the bodily passage. Referring to FIG. 4b, the proximal end 45 of the spiral expandable stent 42 may be connected to an inflation lumen 49 of the carrier or to an external inflation tube running along the carrier.

Figures 3A, 3B, 3C:
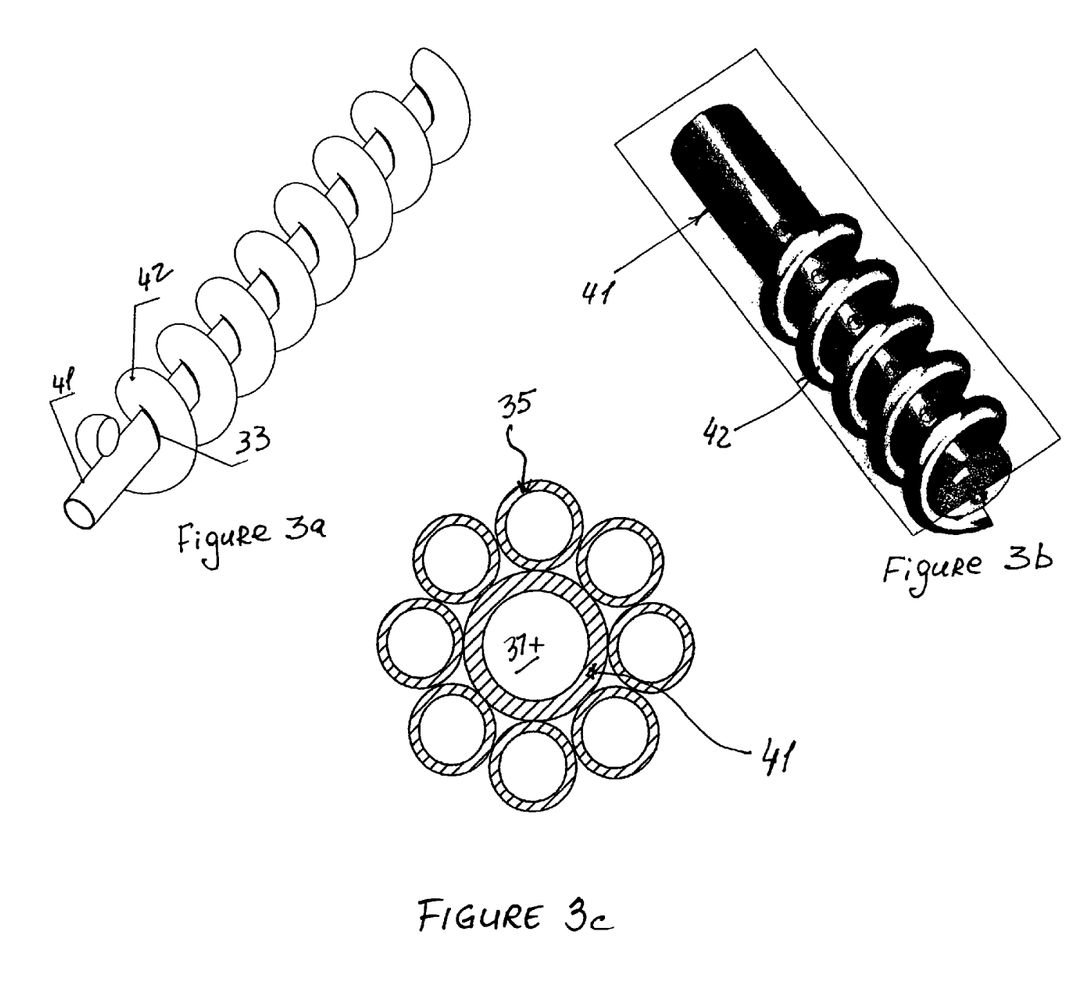
FIGS. 3a and 3b show an embodiment in which the stent forms a spiral about the carrier.
FIG. 3c shows an embodiment, in which a plurality of expandable stents are circumferentially attached to the distal end of the carrier.
Figure 4A:
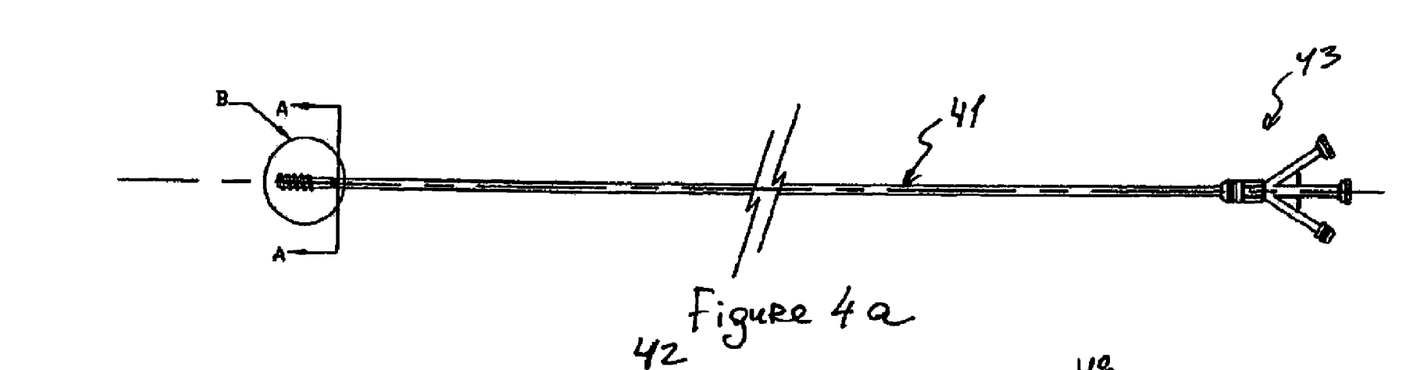
FIGS. 4a-4c depict further detail of the embodiment shown in FIGS. 3a and 3b, in which the stent forms a spiral about the carrier.
Figure 4B:
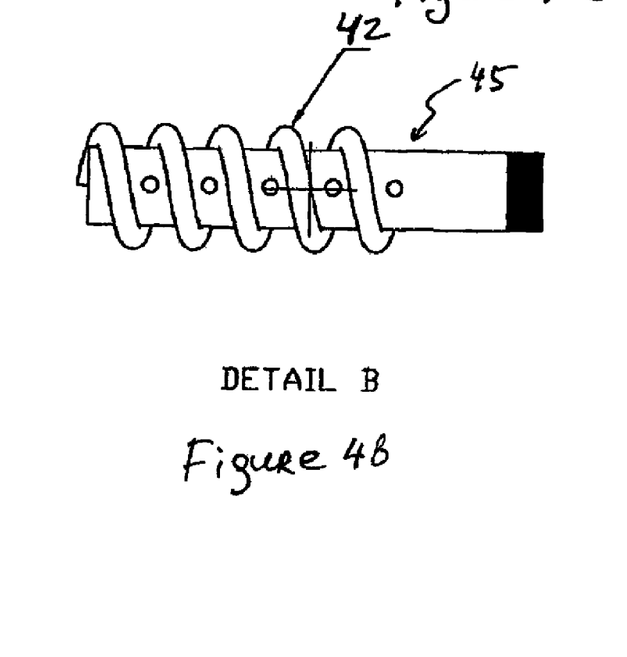
Figure 4C:
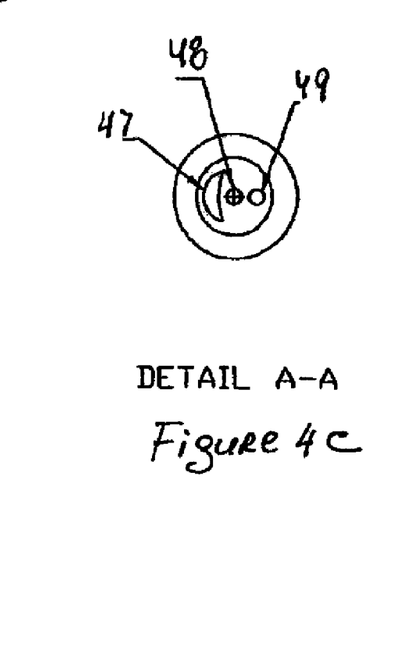

Referring to FIG. 3c, in another embodiment, a plurality of expandable stents 35 are circumferentially attached to the distal end of the carrier 41. These multiple stents are designed to "hug" the carrier 41 during insertion and withdrawal of the stent assembly. The central lumen 37 may be used as a guidewire lumen during insertion and withdrawal of the stent assembly and as a fluid discharge lumen when the stent is inside in the patient. The stents 35 may be fused with or glued to the carrier. This embodiment allows an improved attachment within passage being treated. Additionally, loss of pressure in one individual stent will not render the whole assembly dysfunctional.

As shown in FIGS. 1a-d, the stent 12 may be mounted permanently on the carrier. Those familiar with catheter engineering techniques will recognize numerous methods that can be used to securely and permanently attach the stent 12 to the carrier 11. For example, the stent may be fused with or glued to the carrier.

Alternatively, as shown in FIGS. 5a-5e, the stent 52 may be detachable from the carrier 51. The expandable stent 52 is mounted onto the carrier 51 prior to the insertion into the patient. The stent 52 is designed to be disengaged from the carrier 51 or left engaged with the carrier 51 after it is placed inside the bodily passage. This embodiment allows a withdrawal of the carrier, such as a bulky catheter, from the patient and leaving the expandable stent along with a very small tubing with double function: a) to be acting as a bile discharge tube and b) to be used as a guidewire lumen once the withdrawal of the stent is desired.

The stent used in this embodiment may be made of a material and have a size similar to those described above in reference to permanently attached stents. In one embodiment, the stent 52 has a central tube 55 that serves as a conduit for introduction of the carrier's guidewire/fluid discharge tube. The central tube 55 may be made of thin poly-tetra-fluoroethylene (PTFE). In one embodiment, central tube 55 has an outside diameter in the range of 0.052"-0.056" and inside diameter in the range of 0.048"-0.052".

In one embodiment, the proximal end 54 of the stent houses a valve assembly 56 connected to a port 57. The combination of the valve assembly 56 and the port 57 provides a fluid communication between the internal cavity 501 of the expandable stent 52 and inflation lumen of the carrier 51 for inflation/deflation of the stent. The valve assembly 56 is designed to allow injection of a solution, such as a contrast media, into the expandable stent while preventing retrograde flow from the stent when the carrier 51 is disengaged from the stent 52. In one embodiment, the port 57 is made from silicone or neosprene material with shore hardness in the range of 40-50A and may sustain pressures of up to 25 ata. Optional radiopaque band markers 503 and 504 may be located at the proximal and distal end of the stent to allow visualization of the extremities of the stent under fluoroscopic guidance. The proximal end 54 of the stent 52 may include a flexible outside ring with flap 507 that may be "tucked" within the carrier during the delivery of the stent.

In one embodiment, in which stricture of biliary duct is being treated, the inner cavity 501 of the stent is filled via port 57 and valve assembly 56 by a contrast media solution to a prescribed pressure to achieve an outside diameter of the stent greater by 1-2 mm than the diameter of the biliary duct.

Figures 5A, 5B, 5C:
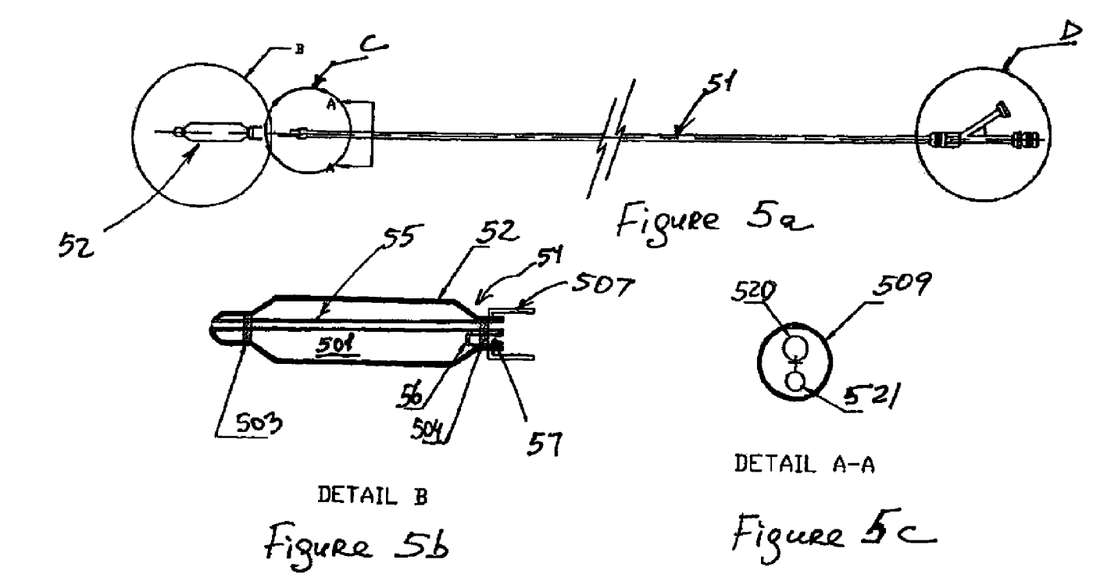
FIGS. 5a-5e show a stent assembly for expanding a bodily passage in a patient and draining a fluid therefrom, in which the stent is detachable from the carrier in accordance with one embodiment of the present invention.

In one embodiment, the carrier 51 comprises a combination of at least two movable concentric tubes. As shown in FIG. 5c, in one embodiment, a first tube 509 forms a drainage lumen 520 and an inflation lumen 521. In another embodiment shown in FIG. 5d, the first tube 509 (not shown for clarity) houses a drainage tube 531 and a an inflation tube 532. The second tube 515 (shown in FIG. 5d but not in FIG. 5c) is a movable member that houses the first tube and is movable over the stent in an expanded form.

Figure 5D:
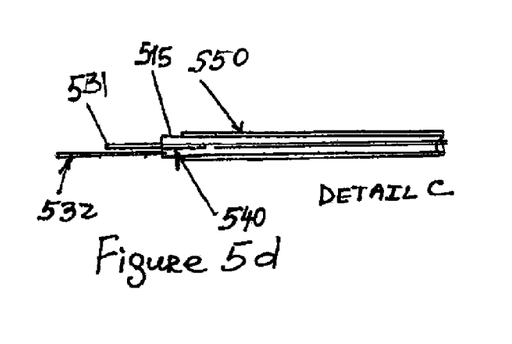
Figure 5E:
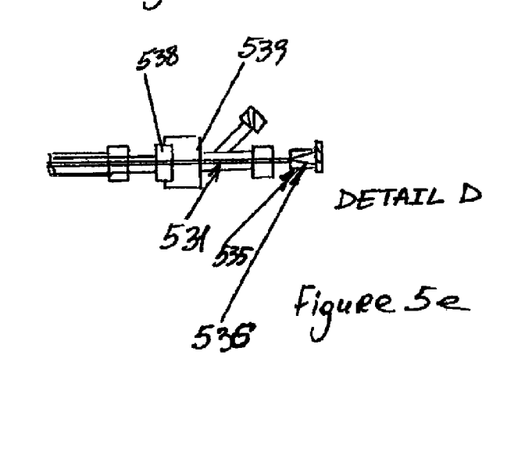

The second tube 515 may be made of Pebax, PE, PTFE or other similar extruded polymeric material in the range of 60-70 D hardness with outside diameter in the range of 5 to 8 inches and inside diameter of 4.5 to 7.5 mm. The proximal end of the second tube 515 may have a short perforated section 540 to allow the tube second tube to ride over the expandable stent. A proximal end of the second tube 531 may be connected to connector 538, which may be connected to a rotating henestatic valve connector 539.

In one embodiment, the drainage lumen 520 or drainage tube 531 is designed to accommodate a guidewire. In one embodiment, the drainage lumen 520 or drainage tube 531 has an internal diameter of 0.042"-0.045" and an outer diameter of 0.048"-0.052".

Prior to the delivery of the stent, the drainage tube 531 is positioned within lumen 55 of the stent. In one embodiment, the drainage tube 531 is designed to act as a guidewire lumen and a fluid discharge channel which will be left in the patient once the expandable stent is placed within the passage to be treated and other parts of the carrier are removed. Inflation lumen 521 or inflation tube 532 communicate through the port 57 and valve assembly 56 with an internal cavity 501 of the stent.

A proximal end of the drainage tube 531 may be connected to a connector 535. In one embodiment, the connector 535 has a tapered cavity 536, which allows the introduction of a Teflon coated guidewire with outside diameter of 0.035" to 0.038".

The carrier may optionally include an outer tube 550 designed as a movable sheath to be able to ride over the second tube 515 and seal it tightly over the proximal end 54 of the expandable stent 52. The outer tube 550 may be made of Pebax, PE, PTFE or other similar polymeric extruded material and may have, for example, an inside diameter in the range of 5.5 to 7.5 mm and outside diameter in the range of 6 to 8 mm.

Figure 6A:
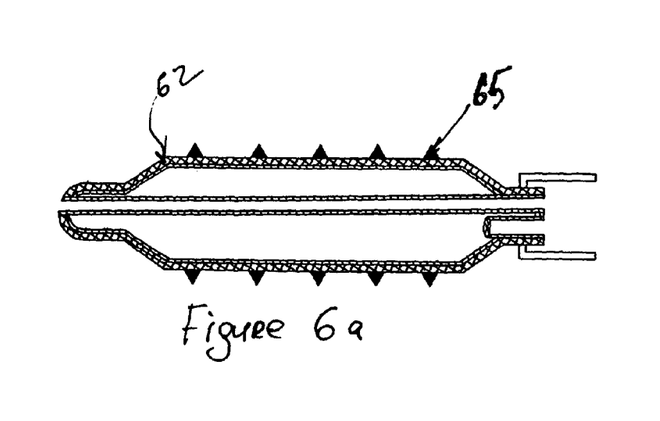
FIGS. 6a-6c show a stent with net and barb structures in accordance with another embodiment of the present invention.
Figure 6B:
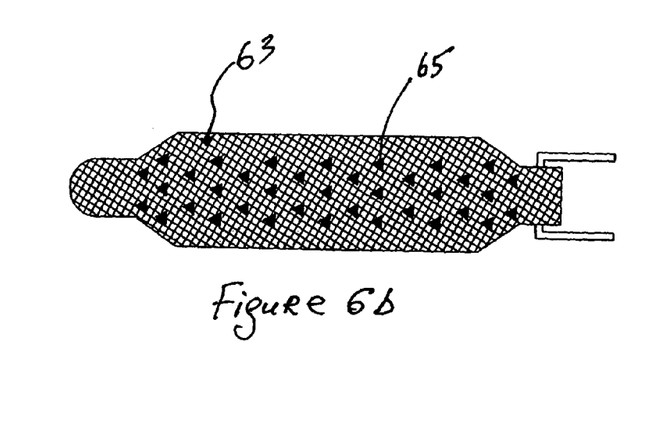
Figure 6C:
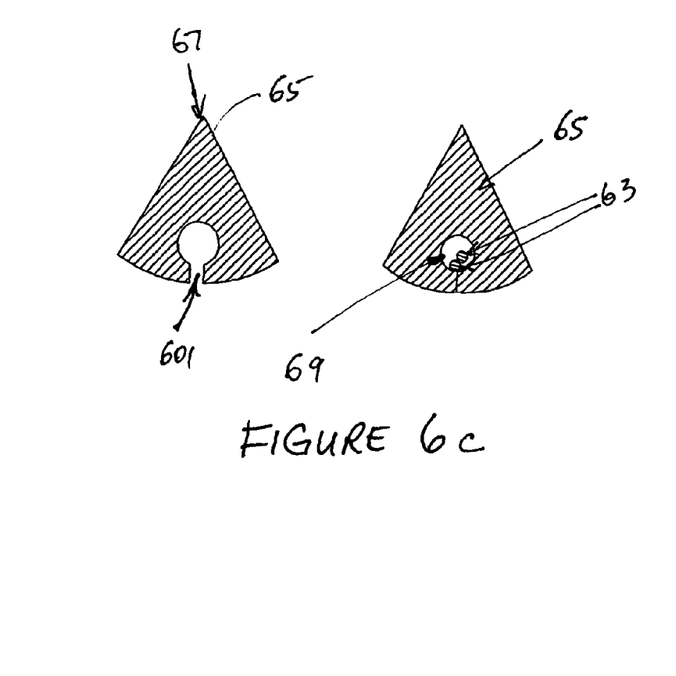

In another embodiment illustrated in FIGS. 6a-6c, a tubular net-like structure 63 is connected to the outside surface of the stent 62. The net-like structure may be a braided net made of thin filament of PTE. For example, 0.006" to 0.008" diameter fiber could be used. This net-kike structure may connect to a multitude of "barb" elements 65. The net-like structure 63 may also be fused with or connected to an outside surface of the expandable stent 62.

The diameter of the net-like structure 63 is designed in such a way that it "hugs" an outside surface of the stent 62 and it could follow its contour after its deflation as well as during its inflation.

The "barb" elements 65 are made of stainless steel or an equivalent material and facilitate engagement of the expandable stent to the inner wall of the bodily passage during deployment. The sharp edge 67 of "barb" elements 65 is positioned toward the inner wall of the passage. After the deployment of the stent, the "barb" elements 65 assure the positioning and the engagement of the expandable stent within the passage while the internal pressure of the expandable stent provides sufficient radial force for the barbs to be engaged within the passage.

In one embodiment, barb elements 65 are connected to the net 63 according to FIG. 6c. The through channel 69, located at the center of barb element 65, is designed to be engaged into the crossing point between the crossing filaments of PE fiber. The nutch 601 will allow the placement of the barb element 65 over the two PE filaments and once that is accomplished the nutch 601 can be crimped to lock the PE filaments into the barb element permanently.

The net-like structure 63 may also be made of a self-expanding metallic stent made of stainless steel, elgiloy or Ni-Ti wires having barb elements such as 65 connected to the outside surface of the expandable structure. In one embodiment, this expandable structure (either the PE braided net or metallic scent) is connected or crimped to the outside diameter of the expandable stent and since this connection is intact, when the expandable biliary scent is deflated, the net structure or the metallic stent will also be forced to "deflate" and consequently disengage the barbs 65 from the internal wall of the bodily passage.

In another aspect, the present invention provides a method of expanding a bodily passage in a patient and draining a fluid therefrom. The method comprises: (a) providing a stent assembly of the present invention; (b) inserting a guidewire into the bodily passage through the drainage lumen of the carrier; (c) advancing the assembly along the guidewire until the assembly reaches a desired location; (d) expanding the stent; and (e) draining the fluid through drainage lumen of the carrier. In one embodiment, the method further comprises a step of retrieving the stent percutaneously. The retrieved stent may be replaced with a new stent, such that the new stent, when expanded, has a size that is larger than the size of the retrieved stent.

In one embodiment, the stent is permanently affixed to the carrier and the method further comprises steps of deflating the stent, removing the assembly over the guidewire, inserting a new assembly over the guidewire, and expanding a new stent of the new assembly. In another embodiment, the stent is detachable from the carrier and the method further comprising a step of disengaging the carrier from the stent after the stent is inflated and removing the carrier over the guidewire. In case of a treatment of a biliary stricture, the stent assembly of the present invention may be inserted into a biliary duct using conventional techniques such as Percutaneous Transhepatic Cholangiography (PTC) or Endoscopic Retrograde Cholangio-pancreatography (ERCP).

EXAMPLE 1

Clinical Application Of The Biliary Stent[1]

Patient is placed on spine in a decubitus position. The skin is prepared with betadine and the area of interest which is the upper abdomen lower torso on the right side is exposed and surrounded by sterile towels. 1% lidocane local anesthesia is injected in the $10^{th}$ inter-costal space at the mid axillary line on the right side. A 15 cm long flexible 22 gauge needle with an external diameter of 0.8 mm and 30 degree cutting bevel is used for puncture towards the 11th vertebral body. The needle is advanced under direct fluoroscopic control in a parallel fashion to the X-ray table through the liver in the $10^{th}$ inter-costal space toward the body of the $12^{th}$ vertebrae until the tip of the needle reaches the midline at this level under fluoroscopy The stylet of the needle is then removed, and a 10 mm syringe filled with diluted contrast with normal saline (50%) is attached to a clear flexible tubing which is connected to the needle hub. Under fluoroscopic observation, contrast medium is slowly injected with a syringe as the needle is slowly withdrawn from its initial position in the liver. Once a biliary radical is identified, the needle is held in place, bile is aspirated to confirm the position of the needle into the biliary system, then the tubing is disconnected frond the needle.

A 0.018" guidewire with a stiff body and a flexible tip is passed through the 22 gauge needle towards the narrow area of the biliary system. A catheter (4 French, which allow the passage of 0.035 inch guide wire) is introduced over the soft guide wire to dilate the track of the guide-wire from the skin to the liver. A stiff steerable guide wire (0.035 inch) with a flexible tip is introduced into the canula sheath and advanced toward the stenotic area of the biliary system. The guide wire is steered to go through the stricture into the distal common bile duct or across the bilio-enteric anastomosis.

Figure 7A:
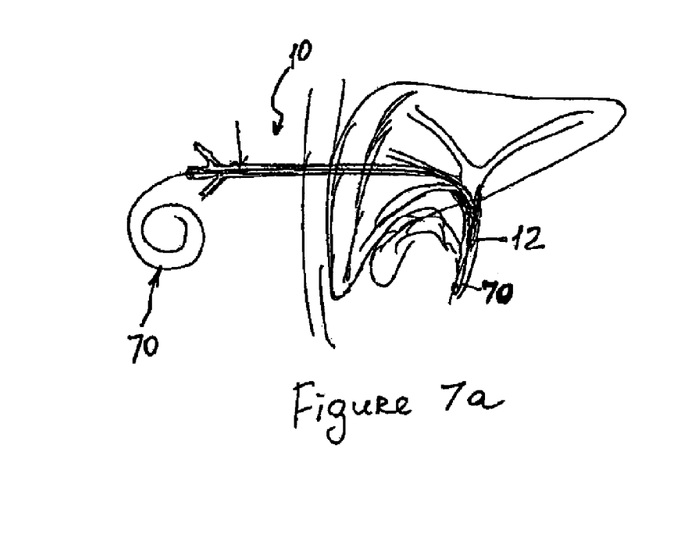
FIGS. 7a and 7b schematically illustrate introduction of the stent assembly of the present invention into a patient.

The canula is withdrawn leaving the guide wire in place across the biliary stricture. Referring to FIG. 7a, the biliary stent assembly 10 of the present invention is then introduced over the guide wire 70 towards the stenotic area and its position is confirmed under fluoroscopy by the extendable stent 12 filled with a contrast solution as well as X-ray markers present on each side of the balloon area (not shown).

Figure 7B:
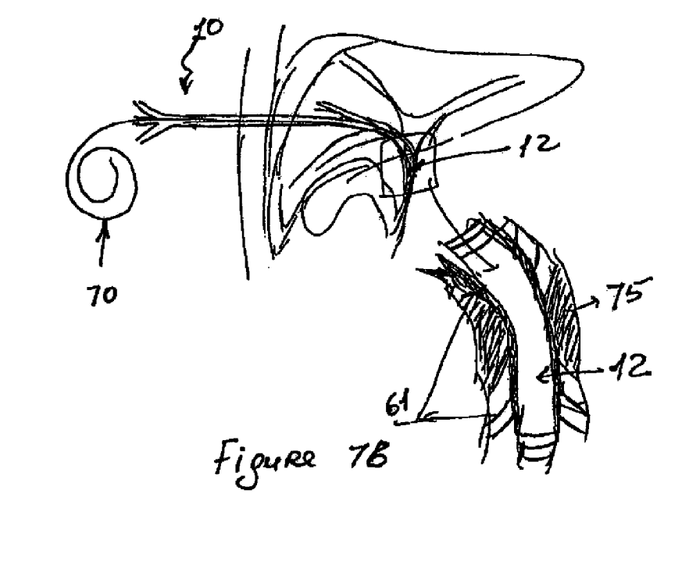
Figure 8A:
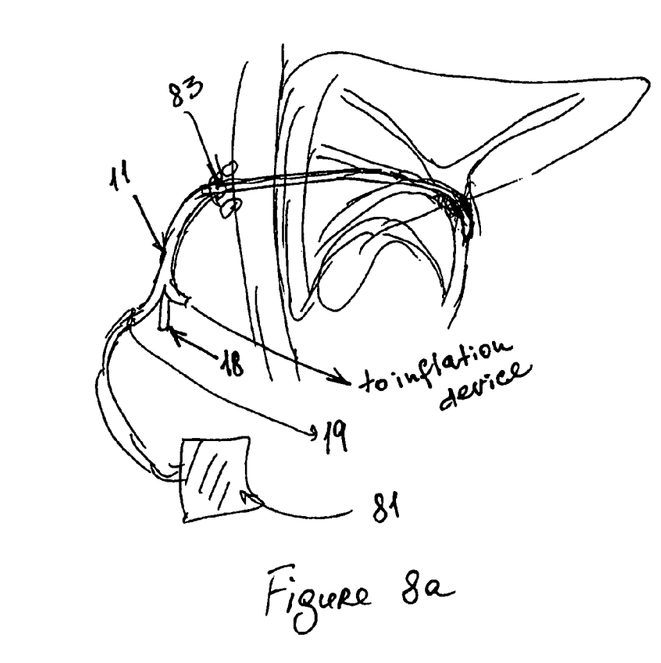
FIGS. 8a and 8b schematically illustrate increasing the size of the stent without removing it from the bodily passage in accordance with an embodiment of the present invention.

Referring to FIG. 7b, when the location of the stent is confirmed under fluoroscopy, the stent 12 is deployed to stabilize the stent in place and to begin dialation of a stricture 75. After deployment, optional barb elements 61 assure the positioning and the engagement of the stent 12. Referring to FIG. 8a, the drainage lumen 17 of the catheter 11 is connected to a bile bag 81. The guidewire is removed and guidewire lumen 18 is capped. The inflation lumen 19 is connected to an inflation device (not shown). The catheter 11 is then sutured to the skin using monofilament suture 83. The inflation device is activated and provides a progressive dilatation of one or of a plurality of successive balloons over 24-48 hours with diluted contrast.

Figure 8B:
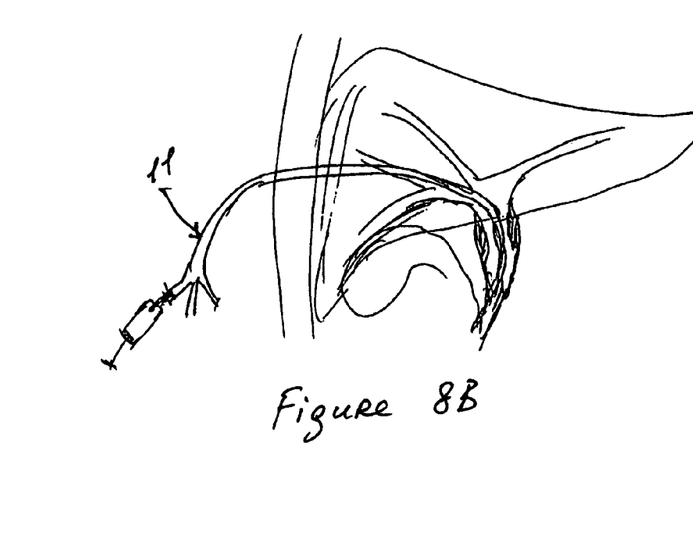

The size of dilatation of the stricture is verified under fluoroscopy in 24-48 hours, and once the appropriate size is reached the balloon is left in place for up to 7 days then deflated progressively. Once the deflation is completed, the size of stricture is reassessed. If residual stricture persists, additional dilatation is performed by adding contrast solution as shown in FIG. 8b. Once the appropriate size is reached the catheter 11 is withdrawn.

The foregoing is meant to illustrate, but not to limit, the scope of the invention. Indeed, those of ordinary skill in the art can readily envision and produce further embodiments, based on the teachings herein, without undue experimentation.

What is claimed is:

1. A stent assembly for expanding a constricted bodily passage in a patient and draining a fluid thereform, the assembly comprising:
   a stent having an inflatable body; and
   an elongated carrier for delivery or retrieval of the stent, the carrier having a distal end and a proximal end, wherein the stent is —circumferentially attached to the distal end of the carrier,
   the carrier comprising a combination of at least two movable tubes, wherein a first tube comprises a drainage lumen and an inflation lumen and a second tube is a movable member that houses the first tube and is movable over the stents in an expanded form wherein the drainage lumen is in fluid communication with the bodily passage and the inflation lumen in fluid communication with the expandable stent such that the stent may be gradually, continuously or intermittently expanded in place to dynamically dilate the constricted passage,and whereby when the bodily passage is dilated by expansion of said stents within said bodily passage, fluid is drained in place via the drainable lumen of said carrier;
   wherein the stent is detachable from the catheter; and
   wherein the second tube has a perforated section to allow the tube to move over the expanded stent.

2. The assembly of claim 1, wherein the drainage lumen is sized to accommodate a removable guidewire.

3. The assembly of claim 1, wherein the carrier further comprises a separate guidewire lumen sized to accommodate a guidewire.

4. The assembly of claim 1, wherein the inflation lumen communicates with an internal cavity of the stent through inflation holes located within an orthogonal projection of the stent onto the inflation lumen of the carrier.

5. The assembly of claim 1, wherein the drainage lumen communicates with the bodily passage through a plurality of drainage holes connecting an outer surface of the carrier with the drainage lumen.

6. The assembly of claim 1, wherein the carrier is a catheter with an outer diameter from 8 to 18 French.

7. The assembly of claim 1, wherein the carrier comprises a plurality of drainage lumens.

8. The assembly of claim 1, wherein the carrier is made from a polymeric biocompatible material with hardness in the range of 80 A to 50 D.

9. The assembly of claim 1, wherein the stent comprises a resilient polymeric material.

10. The assembly of claim 1, wherein an outer diameter of the stent when expanded is larger than an internal diameter of the bodily passage to be treated.

11. The assembly of claim 1, wherein the passage is selected from a group consisting of biliary duct, kidney duct, sinus pathway, intracranial passages and voids, esophagus, urinary tract, gastrointestinal (GI) tract, and the tracheo-bronchial tree.

12. The assembly of claim 11, wherein an outer diameter of the stent is from 4 to 12 mm when expanded.

13. The assembly of claim 11, wherein a length of the stent is from 20 to 100 mm when expanded.

14. The assembly of claim 1, wherein an outer diameter of the stent when expanded is larger than an internal diameter of the bodily passage to be treated by from 1 to 2 mm.

15. The assembly of claim 1, wherein the assembly further comprises a connector attached to the proximal end of the carrier, the connector having a first side arm in a communication with the drainage lumen and a second side arm in a communication with the inflation lumen.

16. The assembly of claim 15, wherein the first side arm is further connected to a fluid collection container.

17. The assembly of claim 15, wherein the second side arm is further removably connected to an inflation device for inflation or deflation of the stent via a valve connector or a three-way stopcock.

18. The assembly of claim 17, wherein the valve connector allows injection of a solution into the expandable stents while preventing retrograde flow of the solution from the stent.

19. The assembly of claim 15, wherein the carrier further comprises a separate guidewire lumen sized to accommodate a guidewire and the connector further comprises a third side arm in a communication with the guidewire lumen of the carrier.

20. The assembly of claim 1, wherein the stent is permanently affixed to the carrier.

21. The assembly of claim 1, wherein the drainage lumen is sized to accommodate a guidewire during insertion of the assembly into the bodily passage.

22. The assembly of claim 1, wherein the drainage lumen is structured to remain connected to the stents and act as a fluid discharge channel when other parts of the carrier are removed.

23. The assembly of claim 1,
wherein the carrier further comprises a third tube capable of moving over the second tube to seal the second tube over the expanded stent.

24. The assembly of claim 1, wherein the stent further comprises a valve assembly for inflation or deflation of the stents, the valve assembly is in a fluid communication with an internal cavity of the stent.

25. The assembly of claim 24, wherein the valve assembly allows injection of a solution into the cavity of the stent while preventing retrograde flow from the stents when the carrier is disengaged from the stent.

26. The assembly of claim 1, wherein the stent further comprises a cylindrical net-like structure.

27. The assembly of claim 26, wherein the net-like structure is fused or connected to an outer surface of the stent.

* * * * *